(12) United States Patent
Bril et al.

(10) Patent No.: US 6,368,823 B1
(45) Date of Patent: Apr. 9, 2002

(54) KV POTASSIUM CHANNEL POLYPEPTIDES AND POLYNUCLEOTIDES

(75) Inventors: Antoine Michel Alain Bril, Rennes; Thierry Paul Gerard Calmels, Pace; Jean-Francois Simon Pierre Faivre, Rennes; Jean-Luc Javre, La Chapelle des Fougeretz; Sabine Rouanet, Betton, all of (FR)

(73) Assignee: SmithKline Beecham Laboratoires Pharmaceutiques, Nanterre Cedex (FR)

( * ) Notice: Subject to any disclaimer, the term of this patent is extended or adjusted under 35 U.S.C. 154(b) by 0 days.

(21) Appl. No.: 09/142,791

(22) PCT Filed: Mar. 23, 1998

(86) PCT No.: PCT/EP98/01901

§ 371 Date: Feb. 2, 1999

§ 102(e) Date: Feb. 2, 1999

(87) PCT Pub. No.: WO98/42833

PCT Pub. Date: Oct. 1, 1998

(30) Foreign Application Priority Data

Mar. 27, 1997 (GB) ............................................. 9706377
Dec. 9, 1997 (EP) ............................................. 97402971
Dec. 11, 1997 (EP) ............................................. 97403007

(51) Int. Cl.[7] ........................ C07K 21/04; C12N 15/00; C12N 5/00; C12N 15/03; C12N 15/06

(52) U.S. Cl. .................. 435/69.1; 435/366; 435/320.1; 435/325; 435/252.3; 536/23.5; 536/23.1

(58) Field of Search .............................. 435/69.1, 320.1, 435/325, 252.3, 366; 530/350; 536/23.5, 23.1; 424/130.1

(56) References Cited

PUBLICATIONS

Dixon et al. "Role of the Kv4.3 $K^+$ Channel in Ventricular Muscle", Circulation Research, vol. 79, pp. 659–668 (1996).
Serôdio et al. "Cloning of a Novel Component of A–Type $K^+$ Channels Operating at Subthreshold Potentials with Unique Expression in Heart and Brain", J. Neurophysiology, vol. 75, pp. 2174–2179 (1996).
Baldwin et al. "Characterization of a Mammalian cDNA for an Inactivating Voltage–Sensitive $K^+$ Channel", Neuron, vol. 7, pp. 471–483 (1991).
GenBank Accession No. U75448. (1996).
GenBank Accession No. U42975. (1996).
GenBank Accession No. S64320. (1993).
Serodio, et al. (1996) J. Neurophysiol., 75(5): 2174–2179.*

* cited by examiner

Primary Examiner—Elizabeth Kemmerer
(74) Attorney, Agent, or Firm—William T. Han; Ratner & Prestia; William T. King

(57) ABSTRACT hKv4.3 polypeptides and polynucleotides and methods for producing such polypeptides by recombinant techniques are disclosed. Also disclosed are methods for utilizing hKv4.3 polypeptides and polynucleotides in the design of protocols for the treatment of cardiac arrhythmias and Alzheimer's disease, among others, and diagnostic assays for such conditions.

8 Claims, 2 Drawing Sheets

SEQUENCE LISTING

<160> NUMBER OF SEQ ID NOS: 14

<210> SEQ ID NO 1
<211> LENGTH: 2104
<212> TYPE: DNA
<213> ORGANISM: HOMO SAPIENS

<400> SEQUENCE: 1

| | | | | | |
|---|---|---|---|---|---|
| atggcggcag | gagttgcagc | ctggctgcct | tttgcccggg | ctgcggccat cggtggatg | 60 |
| ccggtggcca | actgccccat | gcccctggcc | ccggccgaca | agaacaagcg gcaggatgag | 120 |
| ctgattgtcc | tcaacgtgag | tgggcggagg | ttccagacct | ggaggaccac gctggagcgc | 180 |
| tacccggaca | ccctgctggg | cagcacggag | aaggagttct | tcttcaacga ggacaccaag | 240 |
| gagtacttct | tcgaccggga | ccccgaggtg | ttccgctgcg | tgctcaactt ctaccgcacg | 300 |
| gggaagctgc | actacccgcg | ctacgagtgc | atctctgcct | acgacgacga gctggccttc | 360 |
| tacggcatcc | tcccggagat | catcggggac | tgctgctacg | aggagtacaa ggaccgcaag | 420 |
| agggagaacg | ccgagcggct | catggacgac | aacgactcgg | agaacaacca ggagtccatg | 480 |
| ccctcgctca | gcttccgcca | gaccatgtgg | cgggccttcg | agaaccccca caccagcacg | 540 |
| ctggccctgt | tcttctacta | cgtgactggc | ttcttcatcg | ctgtctcggt catcaccaac | 600 |
| gtggtggaga | cggtgccgtg | cggcacggtc | ccgggcagca | aggagctgcc gtgcggggag | 660 |
| cgctactcgg | tggccttctt | ctgcctggac | acggcgtgcg | tcatgatctt caccgtggag | 720 |
| tacctcctgc | ggctcttcgc | ggctcccagc | cgctaccgct | tcatccgcag cgtcatgagc | 780 |
| atcatcgacg | tggtggccat | catgccctac | tacatcggtc | tggtcatgac caacaacgag | 840 |
| gacgtgtccg | gcgccttcgt | cacgctccgg | gtcttccgcg | tcttcaggat cttcaagttt | 900 |
| tcccgccact | cccagggcct | gcggatcctg | ggctacacac | tgaagagctg tgcctccgaa | 960 |
| ctgggctttc | ttctcttctc | cctcaccatg | gccatcatca | tctttgccac tgtgatgttt | 1020 |
| tatgccgaga | agggctcctc | ggccagcaag | ttcacaagca | tccctgcctc gttttggtac | 1080 |
| accattgtca | ccatgaccac | actgggatac | ggagacatgg | tgcctaagac gattgcaggg | 1140 |
| aagatcttcg | gctccatctg | ctccttgagt | ggcgtcctgg | tcattgccct gccagtccct | 1200 |
| gtgattgttt | ccaactttag | ccggatttac | caccagaatc | agagagctga taaacgcagg | 1260 |
| gcacaaaaga | aggcccgcct | tgccaggatc | cgtgtggcca | aaacaggcag ttcgaatgca | 1320 |
| tacctgcaca | gcaagcgcaa | cgggctcctc | aacgaggcgc | tggagctgac gggcacccca | 1380 |
| gaagaggagc | acatgggcaa | gaccacctca | ctcatcgaga | gccagcatca tcacctgctg | 1440 |
| cactgcctgg | aaaaaaccac | taaccacgag | tttattgatg | agcagatgtt tgagcagaac | 1500 |
| tgcatggaga | gttcaatgca | gaactaccca | tccacaagaa | gtccctcact gtccagccac | 1560 |

```
ccaggcctca ctaccacctg ctgctcccgt cgtagtaaga agaccacaca cctgcccaat      1620
tctaacctgc cagctactcg cctgcgcagc atgcaagagc tcagcacgat ccacatccag      1680
ggcagtgagc agccctccct cacaaccagt cgctccagcc ttaatttgaa agcagacgac      1740
ggactgagac caaactgcaa aacatcccag atcaccacag ccatcatcag catccccact      1800
cccccagcgc taaccccaga gggggaaagt cggccacccc ctgccagccc aggcccaac       1860 acgaacattc cttccatagc cagcaatgtt gtcaaggtct ccgccttgta aaaccactgg      1920
acagagggcc agagtgggta gtggggaatg aaggggactg gcatgttggt ggagtggtca      1980
ctgagaccat tccctccccc ctttccccac tatttctgcc tgccccattg taccctagc       2040 actgagactt gtgcctggaa ggaaaaagag gtagcaaagg ggcactgagg ttcaagttgt      2100
tagg                                                                   2104
```

<210> SEQ ID NO 2
<211> LENGTH: 636
<212> TYPE: PRT
<213> ORGANISM: HOMO SAPIENS

<400> SEQUENCE: 2

```
Met Ala Ala Gly Val Ala Ala Trp Leu Pro Phe Ala Arg Ala Ala
 1               5                  10                  15

Ile Gly Trp Met Pro Val Ala Asn Cys Pro Met Pro Leu Ala Pro Ala
                20                  25                  30

Asp Lys Asn Lys Arg Gln Asp Glu Leu Ile Val Leu Asn Val Ser Gly
            35                  40                  45

Arg Arg Phe Gln Thr Trp Arg Thr Thr Leu Glu Arg Tyr Pro Asp Thr
        50                  55                  60

Leu Leu Gly Ser Thr Glu Lys Glu Phe Phe Asn Glu Asp Thr Lys
65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Pro Arg Tyr Glu Cys Ile Ser
            100                 105                 110

Ala Tyr Asp Asp Glu Leu Ala Phe Tyr Gly Ile Leu Pro Glu Ile Ile
        115                 120                 125

Gly Asp Cys Cys Tyr Glu Glu Tyr Lys Asp Arg Lys Arg Glu Asn Ala
    130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
        195                 200                 205

Thr Val Pro Gly Ser Lys Glu Leu Pro Cys Gly Glu Arg Tyr Ser Val
    210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
            260                 265                 270
```

```
Gly Leu Val Met Thr Asn Asn Glu Asp Val Ser Gly Ala Phe Val Thr
            275                 280                 285
Leu Arg Val Phe Arg Val Phe Arg Ile Phe Lys Phe Ser Arg His Ser
        290                 295                 300
Gln Gly Leu Arg Ile Leu Gly Tyr Thr Leu Lys Ser Cys Ala Ser Glu
305                 310                 315                 320
Leu Gly Phe Leu Leu Phe Ser Leu Thr Met Ala Ile Ile Phe Ala
                325                 330                 335
Thr Val Met Phe Tyr Ala Glu Lys Gly Ser Ser Ala Ser Lys Phe Thr
            340                 345                 350
Ser Ile Pro Ala Ser Phe Trp Tyr Thr Ile Val Thr Met Thr Thr Leu
            355                 360                 365
Gly Tyr Gly Asp Met Val Pro Lys Thr Ile Ala Gly Lys Ile Phe Gly
        370                 375                 380
Ser Ile Cys Ser Leu Ser Gly Val Leu Val Ile Ala Leu Pro Val Pro
385                 390                 395                 400
Val Ile Val Ser Asn Phe Ser Arg Ile Tyr His Gln Asn Gln Arg Ala
                405                 410                 415
Asp Lys Arg Arg Ala Gln Lys Lys Ala Arg Leu Ala Arg Ile Arg Val
            420                 425                 430
Ala Lys Thr Gly Ser Ser Asn Ala Tyr Leu His Ser Lys Arg Asn Gly
            435                 440                 445
Leu Leu Asn Glu Ala Leu Glu Leu Thr Gly Thr Pro Glu Glu Glu His
        450                 455                 460
Met Gly Lys Thr Thr Ser Leu Ile Glu Ser Gln His His Leu Leu
465                 470                 475                 480
His Cys Leu Glu Lys Thr Thr Asn His Glu Phe Ile Asp Glu Gln Met
                485                 490                 495
Phe Glu Gln Asn Cys Met Glu Ser Ser Met Gln Asn Tyr Pro Ser Thr
            500                 505                 510
Arg Ser Pro Ser Leu Ser Ser His Pro Gly Leu Thr Thr Thr Cys Cys
        515                 520                 525
Ser Arg Arg Ser Lys Lys Thr Thr His Leu Pro Asn Ser Asn Leu Pro
530                 535                 540
Ala Thr Arg Leu Arg Ser Met Gln Glu Leu Ser Thr Ile His Ile Gln
545                 550                 555                 560
Gly Ser Glu Gln Pro Ser Leu Thr Thr Ser Arg Ser Ser Leu Asn Leu
                565                 570                 575
Lys Ala Asp Asp Gly Leu Arg Pro Asn Cys Lys Thr Ser Gln Ile Thr
            580                 585                 590
Thr Ala Ile Ile Ser Ile Pro Thr Pro Pro Ala Leu Thr Pro Glu Gly
            595                 600                 605
Glu Ser Arg Pro Pro Ala Ser Pro Gly Pro Asn Thr Asn Ile Pro
        610                 615                 620
Ser Ile Ala Ser Asn Val Val Lys Val Ser Ala Leu
625                 630                 635

<210> SEQ ID NO 3
<211> LENGTH: 2072
<212> TYPE: DNA
<213> ORGANISM: HOMO SAPIENS

<400> SEQUENCE: 3
atggcggcag gagttgcagc ctggctgcct tttgcccggg ctgcggccat cgggtggatg    60
```

-continued

```
ccggtggcca actgccccat gcccctggcc ccggccgaca agaacaagcg gcaggatgag    120
ctgattgtcc tcaacgtgag tgggcggagg ttccagacct ggaggaccac gctggagcgc    180
tacccggaca ccctgctggg cagcacggag aaggagttct tcttcaacga ggacaccaag    240
gagtacttct tcgaccggga ccccgaggtg ttccgctgcg tgctcaactt ctaccgcacg    300
gggaagctgc actacccgcg ctacgagtgc atctctgcct acgacgacga gctggccttc    360
tacggcatcc tcccggagat catcggggac tgctgctacg aggagtacaa ggaccgcaag    420
agggagaacg ccgagcggct catggacgac aacgactcgg agaacaacca ggagtccatg    480
ccctcgctca gcttccgcca gaccatgtgg cgggccttcg agaaccccca ccagcacg     540
ctggccctgg tcttctacta cgtgactggc ttcttcatcg ctgtctcggt catcaccaac    600
gtggtggaga cggtgccgtg cggcacggtc ccgggcagca aggagctgcc gtgcggggag    660
cgctactcgg tggccttctt ctgcctggac acggcgtgcg tcatgatctt caccgtggag    720
tacctcctgc ggctcttcgc ggctcccagc cgctaccgct tcatccgcag cgtcatgagc    780
atcatcgacg tggtggccat catgccctac tacatcggtc tggtcatgac caacaacgag    840
gacgtgtccg gcgccttcgt cacgctccgg gtcttccgcg tcttcaggat cttcaagttt    900
tcccgccact cccagggcct gcggatcctg gctacacac tgaagagctg tgcctccgaa    960
ctgggctttc ttctcttctc cctcaccatg gccatcatca tctttgccac tgtgatgttt   1020
tatgccgaga agggctcctc ggccagcaag ttcacaagca tccctgcctc gttttggtac   1080
accattgtca ccatgaccac actgggatac ggagacatgg tgcctaagac gattgcaggg   1140
aagatcttcg gctccatctg ctccttgagt ggcgtcctgg tcattgccct gccagtccct   1200
gtgattgttt ccaactttag ccggatttac caccagaatc agagagctga taaacgcagg   1260
gcacaaaaga aggcccgcct tgccaggatc cgtgtggcca aaacaggcag ttcgaatgca   1320
tacctgcaca gcaagcgcaa cgggctcctc aacgaggcgc tggagctgac gggcaccccca  1380
gaagaggagc acatgggcaa gaccacctca ctcatcgaga gccagcatca tcacctgctg   1440
cactgcctgg aaaaaaccac tgggttgtcc tatcttgtgg atgatcccct gttatctgta   1500
cgaacctcca ccatcaagaa ccacgagttt attgatgagc agatgtttga gcagaactgc   1560
atggagagtt caatgcagaa ctacccatcc acaagaagtc cctcactgtc cagccaccca   1620
ggcctcacta ccacctgctg ctcccgtcgt agtaagaaga ccacacacct gcccaattct   1680
aacctgccag ctactcgcct gcgcagcatg caagagctca gcacgatcca catccagggc   1740
agtgagcagc cctccctcac aaccagtcgc tccagcctta atttgaaagc agacgacgga   1800
ctgagaccaa actgcaaaac atcccagatc accacagcca tcatcagcat ccccactccc   1860
ccagcgctaa ccccagaggg ggaaagtcgg ccacccctg ccagcccagg ccccaacacg   1920
aacattcctt ccatagccag caatgttgtc aaggtctccg ccttgtaaaa catcgaattc   1980
ctgcagcccg ggggatccac tagctctaga gtaccgagct cggatccccc gggccagtgt   2040
gctggaagta ccgagctgga tcgtacccag ct                                  2072
```

<210> SEQ ID NO 4
<211> LENGTH: 655
<212> TYPE: PRT
<213> ORGANISM: HOMO SAPIENS

<400> SEQUENCE: 4

```
Met Ala Ala Gly Val Ala Ala Trp Leu Pro Phe Ala Arg Ala Ala Ala
 1               5                  10                  15
```

```
Ile Gly Trp Met Pro Val Ala Asn Cys Pro Met Pro Leu Ala Pro Ala
             20                  25                  30

Asp Lys Asn Lys Arg Gln Asp Glu Leu Ile Val Leu Asn Val Ser Gly
             35                  40                  45

Arg Arg Phe Gln Thr Trp Arg Thr Thr Leu Glu Arg Tyr Pro Asp Thr
 50              55                  60

Leu Leu Gly Ser Thr Glu Lys Glu Phe Phe Asn Glu Asp Thr Lys
 65                  70                  75                  80

Glu Tyr Phe Phe Asp Arg Asp Pro Glu Val Phe Arg Cys Val Leu Asn
                 85                  90                  95

Phe Tyr Arg Thr Gly Lys Leu His Tyr Pro Arg Tyr Glu Cys Ile Ser
             100                 105                 110

Ala Tyr Asp Asp Glu Leu Ala Phe Tyr Gly Ile Leu Pro Glu Ile Ile
             115                 120                 125

Gly Asp Cys Cys Tyr Glu Glu Tyr Lys Asp Arg Lys Arg Glu Asn Ala
 130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                 165                 170                 175

His Thr Ser Thr Leu Ala Leu Val Phe Tyr Tyr Val Thr Gly Phe Phe
                 180                 185                 190

Ile Ala Val Ser Val Ile Thr Asn Val Val Glu Thr Val Pro Cys Gly
             195                 200                 205

Thr Val Pro Gly Ser Lys Glu Leu Pro Cys Gly Glu Arg Tyr Ser Val
 210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                 245                 250                 255

Ser Val Met Ser Ile Ile Asp Val Val Ala Ile Met Pro Tyr Tyr Ile
                 260                 265                 270

Gly Leu Val Met Thr Asn Asn Glu Asp Val Ser Gly Ala Phe Val Thr
             275                 280                 285

Leu Arg Val Phe Arg Val Phe Arg Ile Phe Lys Phe Ser Arg His Ser
 290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Ile Phe Ala
                 325                 330                 335

Thr Val Met Phe Tyr Ala Glu Lys Gly Ser Ser Ala Ser Lys Phe Thr
                 340                 345                 350

Ser Ile Pro Ala Ser Phe Trp Tyr Thr Ile Val Thr Met Thr Thr Leu
             355                 360                 365

Gly Tyr Gly Asp Met Val Pro Lys Thr Ile Ala Gly Lys Ile Phe Gly
             370                 375                 380

Ser Ile Cys Ser Leu Ser Gly Val Leu Val Ile Ala Leu Pro Val Pro
385                 390                 395                 400

Val Ile Val Ser Asn Phe Ser Arg Ile Tyr His Gln Asn Gln Arg Ala
                 405                 410                 415

Asp Lys Arg Arg Ala Gln Lys Lys Ala Arg Leu Ala Arg Ile Arg Val
             420                 425                 430
```

-continued

```
Ala Lys Thr Gly Ser Ser Asn Ala Tyr Leu His Ser Lys Arg Asn Gly
            435                 440                 445
Leu Leu Asn Glu Ala Leu Glu Leu Thr Gly Thr Pro Glu Glu Glu His
        450                 455                 460
Met Gly Lys Thr Thr Ser Leu Ile Glu Ser Gln His His Leu Leu
465                 470                 475                 480
His Cys Leu Glu Lys Thr Thr Gly Leu Ser Tyr Leu Val Asp Asp Pro
                485                 490                 495
Leu Leu Ser Val Arg Thr Ser Thr Ile Lys Asn His Glu Phe Ile Asp
                500                 505                 510
Glu Gln Met Phe Glu Gln Asn Cys Met Glu Ser Ser Met Gln Asn Tyr
            515                 520                 525
Pro Ser Thr Arg Ser Pro Ser Leu Ser Ser His Pro Gly Leu Thr Thr
        530                 535                 540
Thr Cys Cys Ser Arg Arg Ser Lys Lys Thr Thr His Leu Pro Asn Ser
545                 550                 555                 560
Asn Leu Pro Ala Thr Arg Leu Arg Ser Met Gln Glu Leu Ser Thr Ile
                565                 570                 575
His Ile Gln Gly Ser Glu Gln Pro Ser Leu Thr Thr Ser Arg Ser Ser
            580                 585                 590
Leu Asn Leu Lys Ala Asp Asp Gly Leu Arg Pro Asn Cys Lys Thr Ser
        595                 600                 605
Gln Ile Thr Thr Ala Ile Ile Ser Ile Pro Thr Pro Pro Ala Leu Thr
610                 615                 620
Pro Glu Gly Glu Ser Arg Pro Pro Ala Ser Pro Gly Pro Asn Thr
625                 630                 635                 640
Asn Ile Pro Ser Ile Ala Ser Asn Val Val Lys Val Ser Ala Leu
                645                 650                 655

<210> SEQ ID NO 5
<211> LENGTH: 2104
<212> TYPE: DNA
<213> ORGANISM: HOMO SAPIENS

<400> SEQUENCE: 5
atggcggcag gagttgcagc ctggctgcct tttgcccggg ctgcggccat cgggtgggtg      60
ccggtggcca actgccccat gcccctggcc ccggccgaca gaacaagcg gcaggatgag     120 ctgattgtcc tcaacgtgag tgggcggagg ttccagacct ggaggaccac gctggagcgc     180
tacccggaca ccctgctggg cagcacggag aaggagttct tcttcaacga ggacaccaag     240
gagtacttct cgaccgggga ccccgaggtg ttccgctgcg tgctcaactt ctaccgcacg     300
gggaagctgc actacacgcg ctacgagtgc atctctgcct acgacgacga gctggccttc     360
tacggcatcc tcccggagat catcggggac tgctgctacg aggagtacaa ggaccgcaag     420
agggagaacg ccgagcggct catggacgac aacgactcgg agaacaacca ggagtccatg     480
ccctcgctca gcttccgcca gaccatgtgg cgggccttcg agaacccca caccagcacg     540 ctggccctgg tcttctacta cgtgactggc ttcttcatcg ctgtctcggt catcaccaac     600
gtggtggaga cggtgccgtg cggcacggtc ccgggcagca aggagctgcc gtgcggggag     660
cgctactcgg tggccttctt ctgcctggac acggcgtgcg tcatgatctt caccgtggag     720
tacctcctgc ggctcttcgc ggctcccagc cgctaccgct tcatccgcag cgtcatgagc     780
atcatcgacg tggtggccat catgcccac tacatcggtc tggtcatgac caacaacgag     840
gacgtgtccg gcgccttcgt cacgctccgg gtcttccgcg tcttcaggat ctccaagttt     900
```

-continued

```
tcccgccact cccagggcct gcggatcctg ggctacacac tgaagagctg tgcctccgaa    960
ctgggctttc ttctcttctc cctcaccatg ccatcatca tctttgccac tgtgatgttt   1020
tatgccgaga agggctcctc ggccagcaag ttcacaagca tccctgcctc gttttggtac   1080
accattgtca ccatgaccac actgggatac ggagacatgg tgcctaagac gattgcaggg   1140
aagatcttcg gctccatctg ctccttgagt ggcgtcctgg tcattgccct gccagtccct   1200
gtgattgttt ccaactttag ccggatttac caccagaaac agagagctga taaacgcagg   1260
gcacaaaaga aggcccgcct tgccaggatc cgtgtggcca aaacaggcag ttcgaatgca   1320
tacctgcaca gcaagcgcaa cgggctcctc aacgaggcgc tggagctgac gggcacccca   1380
gaagaggagc acatgggcaa gaccacctca ctcatcgaga ccagcatca tcacctgctg   1440 cactgcctgg aaaaaaccac taaccacgag tttattgatg agcagatgtt tgagcagaac   1500
tgcatggaga gttcaatgca gaactaccca tccacaagaa gtccctcact gtccagccac   1560
ccaggcctca ctaccacctg ctgctcccgt cgtagtaaga agaccacaca cctgcccaat   1620
tctaacctgc cagctactcg cctgcgcagc atgcaagagc tcagcacgat ccacatccag   1680
ggcagtgagc agccctccct cacaaccagt cgctccagcc ttaatttgaa agcagacgac   1740
ggactgagac caaactgcaa acatcccag atcaccacag ccatcatcag catccccact   1800
cccccagcgc taaccccaga gggggaaagt cggccacccc ctgccagccc aggccccaac   1860
acgaacattc cttccatagc cagcaacgtt gtcaaggtct ccgccttgta aaaccactgg   1920
acagagggcc agagtgggta gtggggaatg aaggggactg gcatgttggt ggagtggtca   1980
ctgagaccat tccctccccc ctttccccac tatttctgcc tgccccattg tacccctagc   2040
actgagactt gtgcctggaa ggaaaaagag gtagcaaagg ggcactgagg ttcaagttgt   2100
tagg                                                                2104
```

<210> SEQ ID NO 6
<211> LENGTH: 636
<212> TYPE: PRT
<213> ORGANISM: HOMO SAPIENS

<400> SEQUENCE: 6

```
Met Ala Ala Gly Val Ala Ala Trp Leu Pro Phe Ala Arg Ala Ala
 1               5                  10                  15

Ile Gly Trp Val Pro Val Ala Asn Cys Pro Met Pro Leu Ala Pro Ala
                20                  25                  30

Asp Lys Asn Lys Arg Gln Asp Glu Leu Ile Val Leu Asn Val Ser Gly
            35                  40                  45

Arg Arg Phe Gln Thr Trp Arg Thr Thr Leu Glu Arg Tyr Pro Asp Thr
        50                  55                  60

Leu Leu Gly Ser Thr Glu Lys Glu Phe Phe Asn Glu Asp Thr Lys
    65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Thr Arg Tyr Glu Cys Ile Ser
                100                 105                 110

Ala Tyr Asp Asp Glu Leu Ala Phe Tyr Gly Ile Leu Pro Glu Ile Ile
            115                 120                 125

Gly Asp Cys Cys Tyr Glu Glu Tyr Lys Asp Arg Lys Arg Glu Asn Ala
        130                 135                 140

Glu Arg Leu Met Asp Asp Asn Asp Ser Glu Asn Asn Gln Glu Ser Met
```

-continued

```
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Val Thr Gly Phe Phe
                180                 185                 190

Ile Ala Val Ser Val Ile Thr Asn Val Val Glu Thr Val Pro Cys Gly
                195                 200                 205

Thr Val Pro Gly Ser Lys Glu Leu Pro Cys Gly Arg Tyr Ser Val
    210                 215                 220

Ala Phe Phe Cys Leu Asp Thr Ala Cys Val Met Ile Phe Thr Val Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
                260                 265                 270

Gly Leu Val Met Thr Asn Asn Glu Asp Val Ser Gly Ala Phe Val Thr
                275                 280                 285

Leu Arg Val Phe Arg Val Phe Arg Ile Ser Lys Phe Ser Arg His Ser
    290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Ile Phe Ala
                325                 330                 335

Thr Val Met Phe Tyr Ala Glu Lys Gly Ser Ser Ala Ser Lys Phe Thr
                340                 345                 350

Ser Ile Pro Ala Ser Phe Trp Tyr Thr Ile Val Thr Met Thr Thr Leu
                355                 360                 365

Gly Tyr Gly Asp Met Val Pro Lys Thr Ile Ala Gly Lys Ile Phe Gly
    370                 375                 380

Ser Ile Cys Ser Leu Ser Gly Val Leu Val Ile Ala Leu Pro Val Pro
385                 390                 395                 400

Val Ile Val Ser Asn Phe Ser Arg Ile Tyr His Gln Lys Gln Arg Ala
                405                 410                 415

Asp Lys Arg Arg Ala Gln Lys Lys Ala Arg Leu Ala Arg Ile Arg Val
                420                 425                 430

Ala Lys Thr Gly Ser Ser Asn Ala Tyr Leu His Ser Lys Arg Asn Gly
                435                 440                 445

Leu Leu Asn Glu Ala Leu Glu Leu Thr Gly Thr Pro Glu Glu Glu His
    450                 455                 460

Met Gly Lys Thr Thr Ser Leu Ile Glu Ser Gln His His Leu Leu
465                 470                 475                 480

His Cys Leu Glu Lys Thr Thr Asn His Glu Phe Ile Asp Glu Gln Met
                485                 490                 495

Phe Glu Gln Asn Cys Met Glu Ser Ser Met Gln Asn Tyr Pro Ser Thr
                500                 505                 510

Arg Ser Pro Ser Leu Ser Ser His Pro Gly Leu Thr Thr Thr Cys Cys
                515                 520                 525

Ser Arg Arg Ser Lys Lys Thr Thr His Leu Pro Asn Ser Asn Leu Pro
    530                 535                 540

Ala Thr Arg Leu Arg Ser Met Gln Glu Leu Ser Thr Ile His Ile Gln
545                 550                 555                 560

Gly Ser Glu Gln Pro Ser Leu Thr Thr Ser Arg Ser Ser Leu Asn Leu
                565                 570                 575
```

```
Lys Ala Asp Asp Gly Leu Arg Pro Asn Cys Lys Thr Ser Gln Ile Thr
            580                 585                 590

Thr Ala Ile Ile Ser Ile Pro Thr Pro Pro Ala Leu Thr Pro Glu Gly
        595                 600                 605

Glu Ser Arg Pro Pro Pro Ala Ser Pro Gly Pro Asn Thr Asn Ile Pro
    610                 615                 620

Ser Ile Ala Ser Asn Val Val Lys Val Ser Ala Leu
625                 630                 635

<210> SEQ ID NO 7
<211> LENGTH: 17
<212> TYPE: DNA
<213> ORGANISM: HOMO SAPIENS

<400> SEQUENCE: 7
cacccaccaa catgcca                                                    17

<210> SEQ ID NO 8
<211> LENGTH: 19
<212> TYPE: DNA
<213> ORGANISM: HOMO SAPIENS

<400> SEQUENCE: 8
gcccaaaagc tggagtcac                                                  19

<210> SEQ ID NO 9
<211> LENGTH: 27
<212> TYPE: DNA
<213> ORGANISM: HOMO SAPIENS

<400> SEQUENCE: 9
gttttacaag gcggagacct tgacaac                                         27

<210> SEQ ID NO 10
<211> LENGTH: 22
<212> TYPE: DNA
<213> ORGANISM: HOMO SAPIENS

<400> SEQUENCE: 10
atggcggcag gagttgcagc ct                                              22

<210> SEQ ID NO 11
<211> LENGTH: 28
<212> TYPE: DNA
<213> ORGANISM: HOMO SAPIENS

<400> SEQUENCE: 11
gtcttgccca tgtgctcctc ttctgggg                                        28

<210> SEQ ID NO 12
<211> LENGTH: 28
<212> TYPE: DNA
<213> ORGANISM: HOMO SAPIENS

<400> SEQUENCE: 12
ccgcactggg aagctgcact acccacgc                                        28

<210> SEQ ID NO 13
<211> LENGTH: 28
<212> TYPE: DNA
<213> ORGANISM: HOMO SAPIENS
```

-continued

```
<400> SEQUENCE: 13
ccccagaaga ggagcacatg ggcaagac                                              28

<210> SEQ ID NO 14
<211> LENGTH: 28
<212> TYPE: DNA
<213> ORGANISM: HOMO SAPIENS

<400> SEQUENCE: 14
gtgttgggac ctggactggc aggggtg                                               28
```

US 6,368,823 B1

KV POTASSIUM CHANNEL POLYPEPTIDES AND POLYNUCLEOTIDES

This is the U.S. National Phase of PCT International Application No. PCT/EP98/01901, filed Mar. 23, 1998, which claims the benefit of UK Application No. 9706377.0, filed Mar. 27, 1997, of EP Application No. 97402971.2, filed Dec. 9, 1997, and of EP Application No. 97403007.4, filed Dec. 11, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Kv potassium channel family, hereinafter referred to as hKv4.3. The invention also relates to inhibiting or activating the action of such polynucleotides and polypeptides.

BACKGROUND OF THE INVENTION

The transient outward potassium channel (Ito) is a member of the potassium channel Kv family and is one of the major ionic current involved in the repolarization of the cardiac atrial action potential. In the ventricle, it is responsible for the early repolarization of the action potential. Its electrophysiological characteristics have been demonstrated in human cardiac cell and it is suggested that alterations of its activation and inactivation kinetics play a major role in the genesis of re-entry.

The gene coding for the human channel responsible for this current is still not identified. Amongst the different candidates, it appears that Kv4.3 may be responsible for Ito in the dog and the rat (Circ Res, 1996, 79; 659–668). More recently, a partial fragment of a rat Kv4.3 isoform has been identified (Takimoto et al, Circ Res, 1997, 81:533–539; Ohya S et al, FEBS Letters, 1997,420: 47–53). This comprised an insertion of an extra 19 amino acids. In human heart, the gene coding for Ito has not yet been identified. There remains a need for identification and characterization of further members of the Kv potassium channel family which can play a role in preventing, ameliorating or correcting dysfunctions or diseases, including, but not limited to, cardiac arrhythmias and Alzheimer's disease.

SUMMARY OF THE INVENTION

In one aspect, the invention relates to hKv4.3 polypeptides and recombinant materials and methods for their production. Another aspect of the invention relates to methods for using such hKv4.3 polypeptides and polynucleotides. Such uses include the treatment of cardiac arrhythmias and Alzheimer's disease, among others. In still another aspect, the invention relates to methods to identify agonists and antagonists using the materials provided by the invention, and treating conditions associated with hKv4.3 imbalance with the identified compounds. Yet another aspect of the invention relates to diagnostic assays for detecting diseases associated with inappropriate hKv4.3 activity or levels.

DESCRIPTION OF THE INVENTION

Definitions

Figure 1:
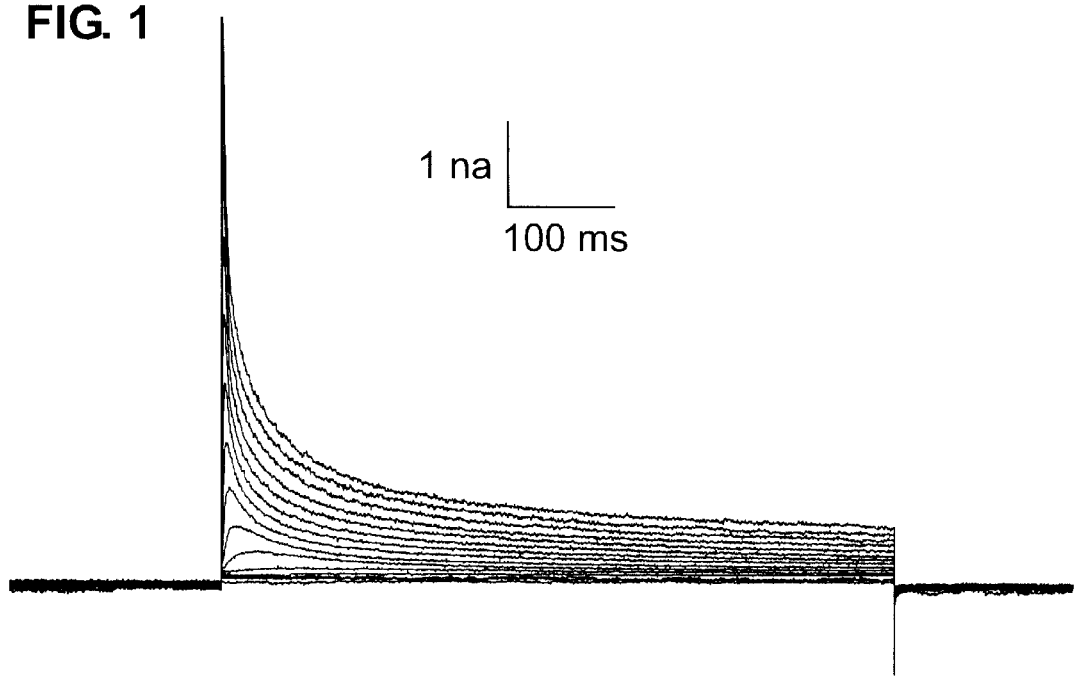
FIG. 1 is a graph showing macroscopic potassium currents flowing through hKv4.3 channels in HEK293 transfected cells.

The following definitions are provided to facilitate understanding of certain terms used frequently herein.

"hKv4.3" refers, among others, generally to a polypeptide having the amino acid sequence set forth in SEQ ID NO:2 or SEQ ID NO:4 or an allelic variant thereof.

"hKv4.3 activity or hKv4.3 polypeptide activity" or "biological activity of the hKv4.3 or hKv4.3 polypeptide" refers to the metabolic or physiologic function of said hKv4.3 including similar activities or improved activities or these activities with decreased undesirable side-effects. Also included are antigenic and immunogenic activities of said hKv4.3.

"hKv4.3 gene" refers to a polynucleotide having the nucleotide sequence set forth in SEQ ID NO:1 or SEQ ID NO:3 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S.F. et al., *J. Molec. Biol.* 215: 403–410 (1990). The BLAST X program is publicly available from NCBI and other sources (BLAST Manual, Altschul, S., et al., NCBI NLM NIH Bethesda, MD 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, *J. Mol Biol.* 48: 443–453 (1970)
   Comparison matrix: BLOSSUM62 from Hentikoff and Hentikoff, *Proc. Natl. Acad. Sci. USA*. 89:10915–10919 (1992)
   Gap Penalty: 12
   Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:

1) Algorithm: Needleman and Wunsch, *J. Mol Biol.* 48: 443–453 (1970)
   Comparison matrix: matches=+10, mismatch=0
   Gap Penalty: 50
   Gap Length Penalty: 3

A program useful with these parameters is publicly available as the "gap" program from Genetics Computer Group, Madison Wis. The aforementioned parameters are the default parameters for polynucleotide comparisons. By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO: 1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 95%, etc., and wherein any non-integer product of Xn and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

Polypeptides of the Invention

In one aspect, the present invention relates to hKv4.3 polypeptides (or hKv4.3 proteins). The hKv4.3 polypeptides include the polypeptides of SEQ ID NO:2 and SEQ ID NO:4; as well as polypeptides comprising the amino acid sequences of SEQ ID NO:2 or SEQ ID NO:4. The polypeptide of SEQ ID NO:4 is an isoform of the polypeptide of SEQ ID NO:2, having an additional 19 amino acids (GLSYLVDDPLLSVRTSTIK) inserted between amino acids 487 and 488.

The hKv4.3 polypeptides further include polypeptides comprising an amino acid sequence which have at least 99% identity to that of SEQ ID NO:2 over its entire length. Also included within hKv4.3 polypeptides are polypeptides having the amino acid sequence which has at least 99% identity to the polypeptide having the amino acid sequence of SEQ ID NO:2 over its entire length.

The hKv4.3 polypeptides further include polypeptides comprising an amino acid sequence which have at least 97% identity, preferably 98% identity, more preferably at least 99% identity, to that of SEQ ID NO:4 over its entire length. Also included within hKv4.3 polypeptides are polypeptides having the amino acid sequence which has at least 97% identity, preferably 98% identity, more preferably at least 99% identity, to the polypeptide having the amino acid sequence of SEQ ID NO:4 over its entire length.

Preferably hKv4.3 polypeptide exhibit at least one biological activity of hKv4.3287.

The hKv4.3 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the hKv4.3 polypeptides are also included in the invention. A fragment is a polypeptide having an amino acid sequence that entirely is the same as part, but not all, of the amino acid sequence of the aforementioned hKv4.3 polypeptides. As with hKv4.3 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of hKv4.3 polypeptide. In this context "about" includes the particularly recited ranges larger or smaller by several, 5, 4, 3, 2 or I amino acid at either extreme or at both extremes.

Preferred fragments include, for example, truncation polypeptides having the amino acid sequence of hKv4.3 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate hKv4.3 activity, including those with a similar activity or an improved activity, or with a decreased undesirable activity. Also included are those that are antigenic or immunogenic in an animal, especially in a human.

Preferably, all of these polypeptide fragments retain the biological activity of the hKv4.3, including antigenic activity. Among the most preferred fragment is that having the amino acid sequence of SEQ ID NO:4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The hKv4.3 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to hKv4.3 polynucleotides. hKv4.3 polynucleotides include isolated polynucleotides which encode the hKv4.3 polypeptides and fragments, and polynucleotides closely related thereto.

More specifically, hKv4.3 polynucleotide of the invention include a polynucleotide comprising the nucleotide sequence contained in SEQ ID NO: 1 encoding a hKv4.3 polypeptide of SEQ ID NO:2, and a polynucleotide having the particular sequence of SEQ ID NOS:1. hKv4.3 polynucleotides further include a polynucleotide comprising a nucleotide sequence that has at least 93% identity over its entire length to a nucleotide sequence encoding the hKv4.3 polypeptide of SEQ ID NO:2, and a polynucleotide comprising a nucleotide sequence that is at least 93% identical, preferably 95% identical, to that of SEQ ID NO:1 over its entire length. Furthermore, those with at least 97% are more preferred and those with at least 98–99% are highly preferred, with at least 99% being the most preferred.

In addition, hKv4.3 polynucleotides of the invention include a polynucleotide comprising the nucleotide sequence contained in SEQ ID NO:3 encoding a hKv4.3 polypeptide of SEQ ID NO: 4, and a polynucleotide having the particular sequence of SEQ ID NOS:3. hKv4.3 polynucleotides further include a polynucleotide comprising a nucleotide sequence that has at least 92% identical, preferably at least 95% identical, over its entire length to a nucleotide sequence encoding the hKv4.3 polypeptide of SEQ ID NO:4, and a polynucleotide comprising a nucleotide sequence that is at least 92% identical, preferably at least 95% identical, to that of SEQ ID NO:3 over its entire length. Furthermore, those with at least 97% are more preferred and those with at least 98–99% are highly preferred, with at least 99% being the most preferred.

Also included under hKv4.3 polynucleotides are a nucleotide sequence which has sufficient identity to a nucleotide sequence contained in SEQ ID NO: 1 or SEQ ID NO:3 to hybridize under conditions useable for amplification or for use as a probe or marker. The invention also provides polynucleotides which are complementary to such hKv4.3 polynucleotides.

hKv4.3 of the invention is structurally related to other proteins of the Kv potassium channel family, as shown by the results of sequencing the cDNA encoding human hKv4.3. The cDNA sequence of SEQ ID NO:1 contains an open reading frame (nucleotide number 1 to 1908) encoding a polypeptide of 636 amino acids of SEQ ID NO:2. The amino acid sequence of SEQ ID NO:2 has about 99% identity (using Bestfit) in 636 amino acid residues with rat Kv4.3 (Dixon et al., Circulation Research, 79: 659–668, 1996). Furthermore, the polypeptide of SEQ ID NO:2 is 77% identical to rat Kv4.2 over 630 amino acid residues (Baldwin,T.J. et al., Neuron 7: 471–483 1991). Furthermore, the polypeptide of SEQ ID NO:2 is 99% identical to rat Kv4.3 over 636 amino acid residues (Serodio et al., *J. Neurophysiology*, 75:2174–2179, 1996). Nucleotide sequence of SEQ ID NO:1 has about 92% identity (using Bestfit) in 1913 nucleotide residues with rat Kv4.3 (Dixon et al., Circulation Research, 79: 659–668, 1996). Furthermore, the polynucleotide of SEQ ID NO:1 is 73% identical to rat Kv4.2 over 1843 nucleotide base residues (Baldwin, T. J. et al., Neuron 7: 471–483 1991). Furthermore, the polynucleotide of SEQ ID NO:1 is 91% identical to rat Kv4.3 over 1913 nucleotide base residues (Serodio et al., *J. Neurophysiology*, 75:2174–2179, 1996).

The cDNA sequence of SEQ ID NO:3 contains an open reading frame (nucleotide number I to 1965) encoding a polypeptide of 655 amino acids of SEQ ID NO:2. Amino acid sequence of SEQ ID NO:4 has about 97% identity (using GCG pileup) in 655 amino acid residues with rat Kv4.3 (Dixon et al., Circulation Research, 79: 659–668, 1996). Furthermore, hKv43 (SEQ ID NO:4) is 71% identical to rat Kv4.2 over 655 amino acid residues (Baldwin, T. J. et al., Neuron 7: 471–483 1991). Furthermore, the polypeptide of SEQ ID NO:4 is 96% identical to rat Kv4.3 over 655 amino acid residues (Serodio et al., *J.Neurophysiology,* 75:2174–2179, 1996). Nucleotide sequence of SEQ ID NO:3 has about 91% identity (using Bestfit) in 1932 nucleotide residues with rat Kv4.3 (Dixon et al., Circulation Research, 79: 659–668, 1996). Furthermore, nucleotide sequence of SEQ ID NO:3 is 72% identical to rat Kv4.2 over 1843 nucleotide base residues (Baldwin, T. J. et al., Neuron 7: 471483 1991). Furthermore, nucleotide sequence of SEQ ID NO:3 is 90% identical to rat Kv4.3 over 1913 nucleotide base residues (Serodio et al., *J. Neurophysiology*, 75:2174–2179, 1996).

The hKv4.3 polypeptides and polynucleotides of the present invention are expected to have, inter alia, similar biological functions/properties to their homologous polypeptides and polynucleotides.

The nucleotide sequence encoding hKv4.3 polypeptide of SEQ ID NO:2 or 4 may be identical to the polypeptide encoding sequence contained in SEQ ID NO:1 (nucleotide number 1 to 1908 of SEQ ID NO:1) SEQ ID NO:3, or it may be a sequence, which as a result of the redundancy (degeneracy) of the genetic code, also encodes the polypeptide of SEQ ID NO:2 or SEQ ID NO:4, respectively.

The present invention also relates to polynucleotide and polypeptide sequences which were first identified prior to the determination of the corresponding full length sequences of SEQ ID NO: 113 and SEQ ID NO:2/4.

Accordingly, in a further aspect, the present invention provides for an isolated polynucleotide comprising:

(a) a nucleotide sequence which has at least 92% identity, preferably at least 93% identity, more preferably at least 94% identity, yet more preferably at least 95% identity, even more preferably at least 97–99% identity to SEQ ID NO:5 over the entire length of SEQ ID NO:5;

(b) a nucleotide sequence which has at least 92% identity, preferably at least 93% identity, more preferably at least 94% identity, yet more preferably at least 95% identity, even more preferably at least 97–99% identity, to SEQ ID NO:5 over the entire length of SEQ ID NO:5;

(c) the polynucleotide of SEQ ID NO:5; or (d) a nucleotide sequence encoding a polypeptide which has at least 92% identity, preferably at least 93% identity, more preferably at least 94% identity, yet more preferably at least 95% identity, even more preferably at least 97–99% identity, to the amino acid sequence of SEQ ID NO:6, over the entire length of SEQ ID NO:6; as well as the polynucleotide of SEQ ID NO:5.

The present invention further provides for a polypeptide which:

(a) comprises an amino acid sequence which has at least 98% identity, preferably at least 99% identity, to that of SEQ ID NO:6 over the entire length of SEQ ID NO:6;

(b) has an amino acid sequence which is at least 98% identity, preferably at least 99% identity, to the amino acid sequence of SEQ ID NO:6 over the entire length of SEQ ID NO:6;

(c) comprises the amino acid of SEQ ID NO:6; and (d) is the polypeptide of SEQ ID NO:6;

as well as polypeptides encoded by a polynucleotide comprising the sequence contained in SEQ ID NO:5.

The nucleotide sequence of SEQ ID NO:5 and the peptide sequence encoded thereby are derived from EST (Expressed Sequence Tag) sequences. It is recognised by those skilled in the art that there will inevitably be some nucleotide sequence reading errors in EST sequences (see Adams, M. D. et at, Nature 377 (supp) 3, 1995). Accordingly, the nucleotide sequence of SEQ ID NO:3 and the peptide sequence encoded therefrom are therefore subjec to the same inherent limitations in sequence accuracy. Furthermore, the peptide sequence encoded by SEQ ID NO:5 comprises a region of identity or close homology and/or close structural similarity (for example a conservative amino acid difference) with the closest homologous or structurally similar protein. SEQ ID NOs:2 and 6 have the following mismatches: aa 20, M/V; aa106, P/T; aa298, F/S; aa 413; N/K.

The cDNA sequence of SEQ ID NO:5 contains an open reading frame encoding a polypeptide of 636 amino acids. Amino acid sequence of SEQ ID NO:6 has about 98% identity (using LASAGENE biocomputing software for windows) in 636 amino acid residues with rat Kv4.3 potassium channel (Circulation Reasearcb 1996, 79, 659). Nucleotide sequence of SEQ ID NO:5 has about 91% identity (using LASAGENE biocomputing software for windows ) in 1914 nucleotide residues with rat Kv4.3 potassium channel (Circulation Reasearch 1996, 79, 659).

One polynucleotide of the present invention encoding hKv4.3 may be obtained using standard cloning and screening, from a cDNA library derived from mRNA in cells of human Human heart and brain using the expressed sequence tag (EST) analysis (Adams, M. D., et al. *Science* (1991) 252:1651–1656; Adams, M. D. et al., *Nature* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When the polynucleotides of the invention are used for the recombinant production of hKv4.3 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Nat Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding hKv4.3 variants comprising the amino acid sequence of hKv4.3 polypeptide of SEQ ID NO:2 in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO: 1 or a fragment thereof (including that of SEQ ID NO:3), may be used as hybridization probes for cDNA and genomic DNA, to isolate full-length cDNAs and genomic clones encoding hKv4.3 polypeptide and to isolate cDNA and genomic clones of other genes (including genes encoding homologs and orthologs from species other than human) that have a high sequence similarity to the hKv4.3 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding hKv4.3 polypeptide, including homologs and orthologs from species other than human, comprises the steps of screening an appropriate library under stingent hybridization conditions with a labeled probe having the SEQ ID NO:1 or a fragment thereof (including that of SEQ ID NO:3), and isolating full-length cDNA and genomic clones containing said polynucleotide sequence. Such hybridization techniques are well known to those of skill in the art Thus in another aspect, hKv4.3 polynucleotides of the present invention further include a nucleotide sequence comprising a nucleotide sequence that hybridize under stringent condition to a nucleotide sequence having SEQ ID NO: 1 or a fragment thereof (including that of SEQ ID NO:3). Also included with hKv4.3 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardfs solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacilus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the hKv4.3 polypeptide is to be expressed for use in screening assays, generally, it is preferred that the polypeptide be produced at the surface of the cell. In this event, the cells may be harvested prior to use in the screening assay. If hKv4.3 polypeptide is secreted into the medium, the medium can be recovered in order to recover and purify the polypeptide; if produced intracellularly, the cells must first be lysed before the polypeptide is recovered. hKv4.3 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of hKv4.3 polynucleotides for use as diagnostic reagents. Detection of a mutated form of hKv4.3 gene associated with a dysfunction will provide a diagnostic tool that can add to or define a diagnosis of a disease or susceptibility to a disease which results from under-expression, over-expression or altered expression of hKv4.3. Individuals carrying mutations in the hKv4.3 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled hKv4.3 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85:4397–4401. In another embodiment, an array of oligonucleotides probes comprising hKv4.3 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to cardiac arrhythmias and Alzheimer's disease through detection of mutation in the hKv4.3 gene by the methods described.

In addition, cardiac arrhythmias and Alzheimer's disease, can be diagnosed by methods comprising determining from a sample derived from a subject an abnormally decreased or increased level of hKv4.3 polypeptide or hKv4.3 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an hKv4.3 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly cardiac arrhythmias and Alzheimer's disease, which comprises:

(a) a hKv4.3 polynucleotide, preferably the nucleotide sequence of SEQ ID NO:1, or a fragment thereof;

(b) a nucleotide sequence complementary to that of (a);

(c) a hKv4.3 polypeptide, preferably the polypeptide of SEQ ID NO:2, or a fragment thereof; or (d) an antibody to a hKv4.3 polypeptide, preferably to the polypeptide of SEQ ID NO:2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the hKv4.3 polypeptides. The term "immunospecific" means that the antibodies have substantiall greater affinity for the polypeptides of the invention than their affinity for other related polypeptides in the prior art.

Antibodies generated against the hKv43 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against hKv4.3 polypeptides may also be employed to treat cardiac arrhythmias and Alzheimer's disease, among others.

Vaccines

Another aspect of the invention relates to a method for inducing an immunological response in a mammal which comprises inoculating the mammal with hKv4.3 polypeptide, or a fragment thereof, adequate to produce antibody and/or T cell immune response to protect said animal from cardiac arrhythmias and Alzheimer's disease, among others. Yet another aspect of the invention relates to a method of inducing immunological response in a mammal which comprises, delivering hKv4.3 polypeptide via a vector directing expression of hKv4.3 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a hKv4.3 polypeptide wherein the composition comprises a hKv4.3 polypeptide or hKv4.3 gene. The vaccine formulation may further comprise a suitable carrier. Since hKv4.3 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The hKv4.3 polypeptide of the present invention may be employed in a screening process for compounds which activate (agonists) or inhibit activation of (antagonists, or otherwise called inhibitors) the hKv4.3 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

hKv4.3 polypeptides are responsible for many biological finctions, including many pathologies. Accordingly, it is desirous to find compounds and drugs which stimulate hKv4.3 polypeptide on the one hand and which can inhibit the function of hKv4.3 polypeptide on the other hand. In general, agonists are employed for therapeutic and prophylactic purposes for such conditions as cardiac arrhythmias and Alzheimer's disease. Antagonists may be employed for a variety of therapeutic and prophylactic purposes for such conditions as cardiac arrhythmias and Alzheimer's disease.

In general, such screening procedures may involve using appropriate cells which express the hKv4.3 polypeptide or respond to hKv4.3 polypeptide of the present invention. Such cells include cells from mammals, yeast, Drosophila or *E. coli*. Cells which express the hKv4.3 polypeptide (or cell membrane containing the expressed polypeptide) or respond to hKv4.3 polypeptide are then contacted with a test compound to observe binding, or stimulation or inhibition of a functional response. The ability of the cells which were contacted with the candidate compounds is compared with the same cells which were not contacted for hKv4.3 activity.

These include methods in which ionic currents are recorded using the patch-clamp technique or standard electrophysiological methods and standard binding methods. FLIPR system (Fluorimetric Imaging Plate Reader) may also be considered.

The assays may simply test binding of a candidate compound wherein adherence to the cells bearing the hKv4.3 polypeptide is detected by means of a label directly or indirectly associated with the candidate compound or in an assay involving competition with a labeled competitor. Further, these assays may test whether the candidate compound results in a signal generated by activation of the hKv4.3 polypeptide, using detection systems appropriate to the cells bearing the hKv4.3 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a hKv4.3 polypeptide to form a mixture, measuring hKv4.3 activity in the mixture, and comparing the hKv4.3 activity of the mixture to a standard.

The hKv4.3 cDNA, protein and antibodies to the protein may also be used to configure assays for detecting the effect of added compounds on the production of hKv4.3 mRNA and protein in cells. For example, an ELISA may be constructed for measuring secreted or cell associated levels of hKv4.3 protein using monoclonal and polyclonal antibodies by standard methods known in the art, and this can be used to discover agents which may inhibit or enhance the production of hKv4.3 (also called antagonist or agonist, respectively) from suitably manipulated cells or tissues.

The hKv4.3 protein may be used to identify membrane bound or soluble receptors, if any, through standard receptor binding techniques known in the art. These include, but are not limited to, ligand binding and crosslinking assays in which the hKv4.3 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of hKv4.3 which compete with the binding of hKv4.3 to its receptors, if any. Standard methods for conducting screening assays are well understood in the art.

Examples of potential hKv4.3 polypeptide antagonists include antibodies or, in some cases, oligonucleotides or proteins which are closely related to the ligands, substrates, enzymes, receptors, etc., as the case may be, of the hKv4.3 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for hKv4.3 polypeptides; or compounds which decrease or enhance the production of hKv4.3 polypeptides, which comprises:

(a) a hKv4.3 polypeptide, preferably that of SEQ ID NO:2;

(b) a recombinant cell expressing a hKv4.3 polypeptide, preferably that of SEQ ID NO:2;

(c) a cell membrane expressing a hKv4.3 polypeptide; preferably that of SEQ ID NO:2; or (d) antibody to a hKv4.3 polypeptide, preferably that of SEQ ID NO:2.

It will be appreciated that in any such kit, (a), (b), (c) or (d) may comprise a substantial component.

Prophylactic and Therapeutic Methods

This invention provides methods of treating abnormal conditions such as, cardiac arrhythmias and Alzheimer's disease, related to both an excess of and insufficient amounts of hKv4.3 polypeptide activity.

If the activity of hKv4.3 polypeptide is in excess, several approaches are available. One approach comprises administering to a subject an inhibitor compound (antagonist) as hereinabove described along with a pharmaceutically acceptable carrier in an amount effective to inhibit the function of the hKv4.3 polypeptide, such as, for example, by blocking the binding of ligands, substrates, enzymes, receptors, etc., or by inhibiting a second signal, and thereby alleviating the abnormal condition. In another approach, soluble forms of hKv4.3 polypeptides still capable of binding the ligand, substrate, enzymes, receptors, etc. in competition with endogenous hKv4.3 polypeptide may be administered. Typical embodiments of such competitors comprise fragments of the hKv4.3 polypeptide.

In another approach, soluble forms of hKv4.3 polypeptides still capable of binding the ligand in competition with endogenous hKv4.3 polypeptide may be administered. Typical embodiments of such competitors comprise fragments of the hKv4.3 polypeptide.

In still another approach, expression of the gene encoding endogenous hKv4.3 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administeredperse or the relevant oligomers can be expressed in vivo.

For treating abnormal conditions related to an underexpression of hKv4.3 and its activity, several approaches are also available. One approach comprises administering to a subject a therapeutically effective amount of a compound which activates hKv4.3 polypeptide, i.e., an agonist as described above, in combination with a pharmaceutically acceptable carrier, to thereby alleviate the abnormal condition. Alternatively, gene therapy may be employed to effect the endogenous production of hKv4.3 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996). Another approach is to administer a therapeutic amount of bKv4.3 polypeptides in combination with a suitable pharmaceutical carrier.

Formulation and Administration

Peptides, such as the soluble form of hKv4.3 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLE 1

Human KV4.3 cDNA Cloning

A partial clone (ATG 975, HGS Est 939345) was initially identified through random searches of the Human Genome data base. This partial clone (406 bp) showed significant homology (Last 45 aa) to the 3' end of the rat KV4.3 gene. To get partial cDNA fragments as well as the full length cDNA: a human heart Marathon ready cDNA (Clontech, Palo Alto, Calif.) was used as a template to amplify:

1. A 1914 bp fragment corresponding to the human KV 4.3 full length cDNA: A first set of PCR experiments was done using reverse (5' CAC CCA CCA ACA TGC CA 3') (SEQ ID NO:7) and forward (5' GCC CAA AAG CTG GAG TCA C 3') (SEQ ID NO:8) primers. Then, after PCR products purification, a second set of PCR experiments was done using reverse (5' GTT TTA CAA GGC GGA GAC CTT GAC AAC 3' based on partial human KV4.3 sequence derived from ATG 975 clone) (SEQ ID NO:9) and forward (5' ATG GCG GCA GGA GTT GCA GCC T 3') (SEQ ID NO:10) gene specific oligonucleotides. One fragment of approximately 2.0 Kb was obtain, blunt ended using pfu DNA polymerase (Stratagene, La Jolla, Calif.) and subcloned into pBluescript KS vector EcoRV digested (Stratagene, La Jolla, Calif.). The sequence of the insert was determined by automated sequencer. A total of 1914 bp were sequenced, this includes an open reading frame encoding a peptide of 636 aa. Fasta analysis show this peptide to have high homology to rat KV4.3 protein. Furthermore hydrophobicity plot of this peptide using the Lasergene Protean program showed the 6 transmembrane spaning hydrophobic domains, typical of all KV family related proteins.

2. One fragment of approximately 1.6 Kb using the same methodology was obtained with forward (5' ATG GCG GCA GGA GTT GCA GCC T 3') (SEQ ID NO:10) and reverse primers (5' GTCTTGCCCATGTGCTCCTCTTCTGGGG 3') (SEQ ID NO:11).

3. One fragment of approximately 1.1 Kb using the same methodology was obtained with forward (5' CCGCACTGG-GAAGCTGCACTACCCACGC 3') (SEQ ID NO:12) and reverse primers (5' GTCTTGCCCATGTGCTCCTCT-TCTGGGG 3') (SEQ ID NO:11).

4. One fragment of approximately 0.55 Kb using the same methodology was obtained with forward (5' CCCCAGAA-GAGGAGCACATGGGCAAGAC 3') (SEQ ID NO:13) and reverse primers (5' GTGTTGGGACCTGGACTG-GCAGGGGGTG 3') (SEQ ID NO:14).

EXAMPLE 2

Electrophysiological Characterization of HKv43 Channel when Expressed in HEK 293 cells Macroscopic potassium currents flowing through hKv4.3 channels in HEK293 transfected cells.

Currents were elicited by 10 mV incremental depolarizations from a membrane holding potential of –80 mV—see FIG. 1

Figure 2:
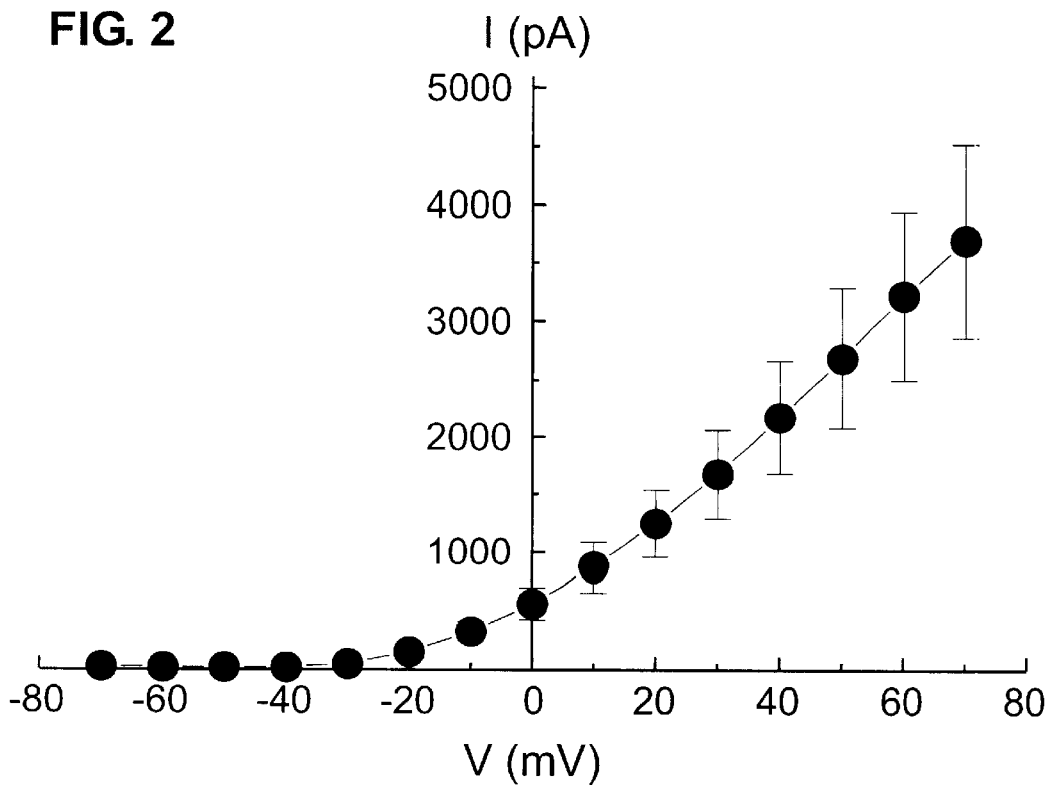
FIG. 2 is a graph showing the current-voltage relationship of current flowing through hKv4.3 channels in HEK293 transfected cells.

Current-voltage relationship of current flowing through hKv4.3 channels in HEK293 transfected cells—see FIG. 2

Figure 3:
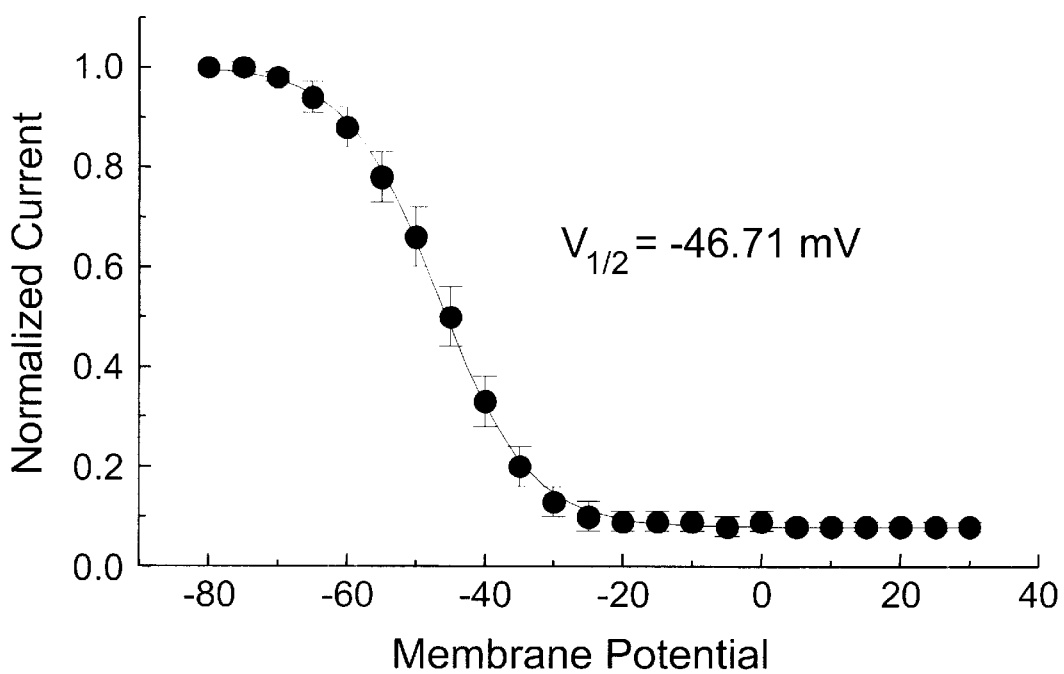
FIG. 3 is a graph showing a steady-state voltage-dependent inactivation curve of current flowing through hKv4.3 channels in HEK293 transfected cells.

Steady-state voltage-dependent inactivation curve of current flowing through hKv4.3 channels in HEK293 transfected cells—see FIG. 3

Figure 4:
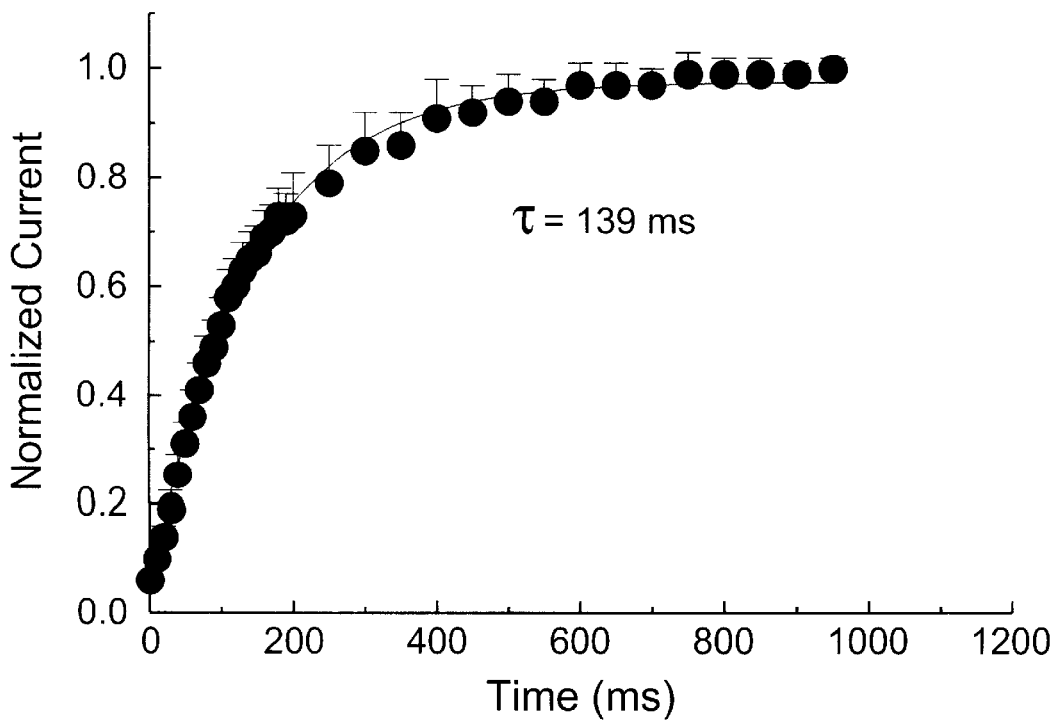
FIG. 4 is a graph showing reactivation property of current flowing through hKv4.3 channels in HEK293 transfected cells.

Reactivation property of current flowing through hKv4.3 channels in HEK293 transfected cells—see FIG. 4

All publications, including but not limited to patents and patent applications, cited in this specification are herein incorporated by reference as if each individual publication were specifically and individually indicated to be incorporated by reference herein as though fully set forth.

SEQ ID NO:1

ATGGCGGCAGGAGTTGCAGCCTGGCTGCCTTTTGCCCGGGCTGCGGCCATCGGGTGGATGCCGGTGGCCAAC

TGCCCCATGCCCCTGGCCCCGGCCGACAAGAACAAGCGGCAGGATGAGCTGATTGTCCTCAACGTGAGTGGG

CGGAGGTTCCAGACCTGGAGGACCACGCTGGAGCGCTACCCGGACACCCTGCTGGGCAGCACGGAGAAGGAG

TTCTTCTTCAACGAGGACACCAAGGAGTACTTCTTCGACCGGGACCCCGAGGTGTTCCGCTGCGTGCTCAAC

TTCTACCGCACGGGGAAGCTGCACTACCCGCGCTACGAGTGCATCTCTGCCTACGACGACGAGCTGGCCTTC

TACGGCATCCTCCCGGAGATCATCGGGGACTGCTGCTACGAGGAGTACAAGGACCGCAAGAGGGAGAACGCC

GAGCGGCTCATGGACGACAACGACTCGGAGAACAACCAGGAGTCCATGCCCTCGCTCAGCTTCCGGGAGACC

ATGTGGCGGGCCTTCGAGAACCCCCACACCAGCACGCTGGCCCTGGTCTTCTACTACGTGACTGGCTTCTTC

ATCGCTGTCTCGGTCATCACCAACGTGGTGGAGACGGTGCCGTGCGGCACGGTCCCGGGCAGCAAGGAGCTG

CCGTGCGGGGAGCGCTACTCGGTGGCCTTCTTCTGCCTGGACACGGCGTGCGTCATGATCTTCACCGTGGAG

TACCTCCTGCGGCTCTTCGCGGCTCCCAGCCGCTACCGCTTCATCCGCAGCGTCATGAGCATCATCGACGTG

GTGGCCATCATGCCCTACTACATCGGTCTGGTCATGACCAACAACGAGGACGTGTCCGGCGCCTTCGTCACG

CTCCGGGTCTTCCGCGTCTTCAGGATCTTCAAGTTTTCCCGCCACTCCCAGGGCCTGCGGATCCTGGGCTAC

ACACTGAAGAGCTGTGCCTCCGAACTGGGCTTTCTTCTCTTCTCCCTCACCATGGCCATCATCATCTTTGCC

ACTGTGATGTTTTATGCCGAGAAGGGCTCCTCGGCCAGCAAGTTCACAAGCATCCCTGCCTCGTTTTGGTAC

ACCATTGTCACCATGACCACACTGGGATACGGAGACATGGTGCCTAAGACGATTGCAGGGAAGATCTTCGGC

TCCATCTGCTCCTTGAGTGGCGTCCTGGTCATTGCCCTGCCAGTCCCTGTGATTGTTTCCAACTTTAGCCGG

ATTTACCACCAGAATCAGAGAGCTGATAAACGCAGGGCACAAAAGAAGGCCCGCCTTGCCAGGATCCGTGTG

GCCAAAACAGGCAGTTCGAATGCATACCTGCACAGCAAGCGCAACGGGCTCCTCAACGAGGCGCTGGAGCTG

ACGGGCACCCCAGAAGAGGAGCACATGGGCAAGACCACCTCACTCATCGAGAGCCAGCATCATCACCTGCTG

CACTGCCTGGAAAAAACCACTAACCACGAGTTTATTGATGAGCAGATGTTTGAGCAGAACTGCATGGAGAGT

TCAATGCAGAACTACCCATCCACAAGAAGTCCCTCACTGTCCAGCCACCCAGGCCTCACTACCACCTGCTGC

TCCCGTCGTAGTAAGAAGACCACACACCTGCCCAATTCTAACCTGCCAGCTACTCGCCTGCGCAGCATGCAA

GAGCTCAGCACGATCCACATCCAGGGCAGTGAGCAGCCCTCCCTCACAACCAGTCGCTCCAGCCTTAATTTG

AAAGCAGACGACGGACTGAGACCAAACTGCAAAACATCCCAGATCACCACAGCCATCATCAGCATCCCCACT

CCCCCAGCGCTAACCCCAGAGGGGAAAGTCGGCCACCCCCTGCCAGCCCAGGCCCCAACACGAACATTCCT

TCCATAGCCAGCAATGTTGTCAAGGTCTCCGCCTTGTAAAACCACTGGACAGAGGGCCAGAGTGGGTAGTGG

GGAATGAAGGGGACTGGCATGTTGGTGGAGTGGTCACTGAGACCATTCCCTCCCCCCTTTCCCCACTATTTC

TGCCTGCCCCATTGTACCCCTAGCACTGAGACTTGTGCCTGGAAGGAAAAAGAGGTAGCAAAGGGGCACTGA

GGTTCAAGTTGTTAGG

SEQ ID NO:2

MAAGVAAWLPFARAAAIGWMPVANCPMPLAPADKNKRQDELIVLNVSGRRFQTWRTTLERYPDTLLGSTEKE

FFFNEDTKEYFFDRDPEVFRCVLNFYRTGKLHYPRYECISAYDDELAFYGILPEIIGDCCYEEYKDRKRENA

ERLMDDNDSENNQESMPSLSFRQTMWRAFENPHTSTLALVFYYVTGFFIAVSVITNVVETVPCGTVPGSKEL

PCGERYSVAFFCLDTACVMIFTVEYLLRLFAAPSRYRFIRSVMSIIDVVAIMPYYIGLVMTNNEDVSGAFVT

LRVFRVFRIFKFSRHSQGLRILGYTLKSCASELGFLLFSLTMAIIIFATVMFYAEKGSSASKFTSIPASFWY

TIVTMTTLGUGDMVPKTIAGKIFGSICSLSGVLVIALPVPVIVSNFSRIYHQNQRADKRRAQKKARLARIRV

AKTGSSNAYLHSKRNGLLNEALELTGTPEEEHMGKTTSLIESQHHHLLHCLEKTTNHEFIDEQMFEQNCMES

SMQNYPSTRSPSLSSHPGLTTTCCSRRSKKTTHLPNSNLPATRLRSMQELSTIHIQGSEQPSLTTSRSSLNL

-continued

KADDGLRPNCKTSQITTAIISIPTPPALTPEGESRPPPASPGPNTNIPSIASNVVKVSAL

SEQ ID NO:3-isoform

ATGGCGGCAGGAGTTGCAGCCTGGCTGCCTTTTGCCCGGGCTGCGGCCATCGGGTGGATGCCGGTGGCCAAC
TGCCCCATGCCCCTGGCCCCGGCCGACAAGAACAAGCGGCAGGATGAGCTGATTGTCCTCAACGTGAGTGGG
CGGAGGTTCCAGACCTGGAGGACCACGCTGGAGCGCTACCCGGACACCCTGCTGGGCAGCACGGAGAAGGAG
TTCTTCTTCAACGAGGACACCAAGGAGTACTTCTTCGACCGGGACCCCGAGGTGTTCCGCTGCGTGCTCAAC
TTCTACCGCACGGGGAAGCTGCACTACCCGCGCTACGAGTGCATCTCTGCCTACGACGACGAGCTGGCCTTC
TACGGCATCCTCCCGGAGATCATCGGGGACTGCTGCTACGAGGAGTACAAGGACCGCAAGAGGGAGAACGCC
GAGCGGCTCATGGACGACAACGACTCGGAGAACAACCAGGAGTCCATGCCCTCGCTCAGCTTCCGGGAGACC
ATGTGGCGGGCCTTCGAGAACCCCCACACCAGCACGCTGGCCCTGGTCTTCTACTACGTGACTGGCTTCTTC
ATCGCTGTCTCGGTCATCACCAACGTGGTGGAGACGGTGCCGTGCGGCACGGTCCCGGGCAGCAAGGAGCTG
CCGTGCGGGAGCGCTACTCGGTGGCCTTCTTCTGCCTGGACACGGCGTGCGTCATGATCTTCACCGTGGAG
TACCTCCTGCGGCTCTTCGCGGCTCCCAGCCGCTACCGCTTCATCCGCAGCGTCATGAGCATCATCGACGTG
GTGGCCATCATGCCCTACTACATCGGTCTGGTCATGACCAACAACGAGGACGTGTCCGGCGCCTTCGTCACG
CTCCGGGTCTTCCGCGTCTTCAGGATCTTCAAGTTTTCCCGCCACTCCCAGGGCCTGCGGATCCTGGGCTAC
ACACTGAAGAGCTGTGCCTCCGAACTGGGCTTTCTTCTCTTCTCCCTCACCATGGCCATCATCATCTTTGCC
ACTGTGATGTTTTATGCCGAGAAGGGCTCCTCGGCCAGCAAGTTCACAAGCATCCCTGCCTCGTTTTGGTAC
ACCATTGTCACCATGACCACACTGGGATACGGAGACATGGTGCCTAAGACGATTGCAGGGAAGATCTTCGGC
TCCATCTGCTCCTTGAGTGGCGTCCTGGTCATTGCCCTGCCAGTCCCTGTGATTGTTTCCAACTTTAGCCGG
ATTTACCACCAGAATCAGAGAGCTGATAAACGCAGGGCACAAAAGAAGGCCCGCCTTGCCAGGATCCGTGTG
GCCAAAACAGGCAGTTCGAATGCATACCTGCACAGCAAGCGCAACGGGCTCCTCAACGAGGCGCTGGAGCTG
ACGGGCACCCCAGAAGAGGAGCACATGGGCAAGACCACCTCACTCATCGAGAGCCAGCATCATCACCTGCTG
CACTGCCTGGAAAAAACCACTGGGTTGTCCTATCTTGTGGATGATCCCCTGTTATCTGTACGAACCTCCACC
ATCAAGAACCACGAGTTTATTGATGAGCAGATGTTTGAGCAGAACTGCATGGAGAGTTCAATGCAGAACTAC
CCATCCACAAGAAGTCCCTCACTGTCCAGCCACCCAGGCCTCACTACCACCTGCTGCTCCCGTCGTAGTAAG
AAGACCACACACCTGCCCAATTCTAACCTGCCAGCTACTCGCCTGCGCAGCATGCAAGAGCTCAGCACGATC
CACATCCAGGGCAGTGAGCAGCCCTCCCTCACAACCAGTCGCTCCAGCCTTAATTTGAAAGCAGACGACGGA
CTGAGACCAAACTGCAAAACATCCCAGATCACCACAGCCATCATCAGCATCCCCACTCCCCCAGCGCTAACC
CCAGAGGGGAAAGTCGGCCACCCCCTGCCAGCCCAGGCCCCAACACGAACATTCCTTCCATAGCCAGCAAT
GTTGTCAAGGTCTCCGCCTTGTAAAACATCGAATTCCTGCAGCCCGGGGATCCACTAGCTCTAGAGTACCG
AGCTCGGATCCCCCGGGCCAGTGTGCTGGAAGTACCGAGCTGGATCGTACCCAGCT

SEQ ID NO:4-isoform

MAAGVAAWLPFARAAAIGWMPVANCPMPLAPADKNKRQDELIVLNVSGRRFQTWRTTLERYPDTLLGSTEKE
FFFNEDTKEYFFDRDPEVFRCVLNFYRTGKLHYPRYECISAYDDELAFYGILPEIIGDCCYEEYKDRKRENA
ERLMDDNDSENNQESMPSLSFRQTMWRAFENPHTSTLALVFYYVTGFFIAVSVITNVVETVPCGTVPGSKEL
PCGERYSVAFFCLDTACVMIFTVEYLLRLFAAPSRYRFIRSVMSIIDVVAIMPYYIGLVMTNNEDVSGAFVT
LRVFRVFRIFKFSRHSQGLRILGYTLKSCASELGFLLFSLTMAIIIFATVMFYAEKGSSASKFTSIPASFWY
TIVTMTTLGUGDMVPKTIAGKIFGSICSLSGVLVIALPVPVIVSNFSRIYHQNQRADKRRAQKKARLARIRV
AKTGSSNAYLHSKRNGLLNEALELTGTPEEEHMGKTTSLIESQHHHLLHCLEKTTGLSYLVDDPLLSVRTST

-continued

IKNHEFIDEQMFEQNCMESSMQNYPSTRSPSLSSHPGLTTTCCSRRSKKTTHLPNSNLPATRLRSMQELSTI

HIQGSEQPSLTTSRSSLNLKADDGLRPNCKTSQITTAIISIPTPPALTPEGESRPPPASPGPNTNIPSIASN

VVKVSAL

SEQ ID NO:5

ATGGCGGCAGGAGTTGCAGCCTGGCTGCCTTTTGCCCGGGCTGCGGCCATCGGGTGGATGCCGGTGGCCAAC

TGCCCCATGCCCCTGGCCCCGGCCGACAAGAACAAGCGGCAGGATGAGCTGATTGTCCTCAACGTGAGTGGG

CGGAGGTTCCAGACCTGGAGGACCACGCTGGAGCGCTACCCGGACACCCTGCTGGGCAGCACGGAGAAGGAG

TTCTTCTTCAACGAGGACACCAAGGAGTACTTCTTCGACCGGGACCCCGAGGTGTTCCGCTGCGTGCTCAAC

TTCTACCGCACGGGGAAGCTGCACTACCCGCGCTACGAGTGCATCTCTGCCTACGACGACGAGCTGGCCTTC

TACGGCATCCTCCCGGAGATCATCGGGGACTGCTGCTACGAGGAGTACAAGGACCGCAAGAGGGAGAACGCC

GAGCGGCTCATGGACGACAACGACTCGGAGAACAACCAGGAGTCCATGCCCTCGCTCAGCTTCCGGGAGACC

ATGTGGCGGGCCTTCGAGAACCCCCACACCAGCACGCTGGCCCTGGTCTTCTACTACGTGACTGGCTTCTTC

ATCGCTGTCTCGGTCATCACCAACGTGGTGGAGACGGTGCCGTGCGGCACGGTCCCGGGCAGCAAGGAGCTG

CCGTGCGGGGAGCGCTACTCGGTGGCCTTCTTCTGCCTGGACACGGCGTGCGTCATGATCTTCACCGTGGAG

TACCTCCTGCGGCTCTTCGCGGCTCCCAGCCGCTACCGCTTCATCCGCAGCGTCATGAGCATCATCGACGTG

GTGGCCATCATGCCCTACTACATCGGTCTGGTCATGACCAACAACGAGGACGTGTCCGGCGCCTTCGTCACG

CTCCGGGTCTTCCGCGTCTTCAGGATCTTCAAGTTTTCCCGCCACTCCCAGGGCCTGCGGATCCTGGCTAC

ACACTGAAGAGCTGTGCCTCCGAACTGGGCTTTCTTCTCTTCTCCCTCACCATGGCCATCATCATCTTTGCC

ACTGGATGTTTTATGCCGAGAAGGGCTCCTCGGCCAGCAAGTTCACAAAGCATCCCTGCCTCGTTTTGGTAC

ACCATTGTCACCATGACCACACTGGGATACGGAGACATGGTGCCTAAGACGATTGCAGGGAAGATCTTCGGC

TCCATCTGCTCCTTGAGTGGCGTCCTGGTCATTGCCCTGCCAGTCCCTGTGATTGTTTCCAACTTTAGCCGG

ATTTACCACCAGAATCAGAGAGCTGATAAACGCAGGGCACAAAAGAAGGCCCGCCTTGCCAGGATCCGTGTG

GCCAAAACAGGCAGTTCGAATGCATACCTGCACAGCAAGCGCAACGGGCTCCTCAACGAGGCGCTGGAGCTG

ACGGGCACCCCAGAAGAGGAGCACATGGGCAAGACCACCTCACTCATCGAGAGCCAGCATCATCACCTGCTG

CACTGCCTGGAAAAAACCACTAACCACGAGTTTATTGATGAGCAGATGTTTGAGCAGAACTGCATGGAGAGT

TCAATGCAGAACTACCCATCCACAAGAAGTCCCTCACTGTCCAGCCACCCAGGCCTCACTACCACCTGCTGC

TCCCGTCGTAGTAAGAAGACCACACACCTGCCCAATTCTAACCTGCCAGCTACTCGCCTGCGCAGCATGCAA

GAGCTCAGCACGATCCACATCCAGGGCAGTGAGCAGCCCTCCCTCACAACCAGTCGCTCCAGCCTTAATTTG

AAAGCAGACGACGGACTGAGACCAAACTGCAAAACATCCCAGATCACCACAGCCATCATCAGCATCCCCACT

CCCCCAGCGCTAACCCCAGAGGGGAAAGTCGGCCACCCCCTGCCAGCCCAGGCCCCAACACGAACATTCCT

TCCATAGCCAGCAACGTTGTCAAGGTCTCCGCCTTGTAAAACCACTGGACAGAGGGCCAGAGTGGGTAGTGG

GGAATGAAGGGGACTGGCATGTTGGTGGAGTGGTCACTGAGACCATTCCCTCCCCCCTTTCCCCACTATTTC

TGCCTGCCCCATTGTACCCCTAGCACTGAGACTTGTGCCTGGAAGGAAAAAGAGGTAGCAAAGGGGCACTGA

GGTTCAAGTTGTTAGG

SEQ ID NO:6

MAAGVAAWLPFARAAAIGWVPVANCPMPLAPADKNKRQDELIVLNVSGRRFQTWRTTLERYPDTL

LGSTEKEFFFNEDTKEYFFDRDPEVFRCVLNFYRTGKLHYTRYECISAYDDELAFYGILPEIIGD

CCYEEYKDRKRENAERLMDDNDSENNQESMPSLSFRQTMWRAFENPHTSTLALVFYYVTGFFIAV

SVITNVVETVPCGTVPGSKELPCGERYSVAFFCLDTACVMIFTVEYLLRLFAAPSRYRFIRSVMS

-continued

IIDVVAIMPYYIGLVMTNNEDVSGAFVTLRVFRVFRISKFSRHSQGLRILGYTLKSCASELGFLL

FSLTMAIIFATVMFYAEKGSSASKFTSIPASFWYTIVTMTTLGYGDMVPKTIAGKIFGSICSLS

GVLVIALPVPVIVSNFSRIYHQKQRADKRRAQKKARLARIRVAKTGSSNAYLHSKRNGLLNEALE

LTGTPEEEHMGKTTSLIESQHHHLLHCLEKTTNHEFIDEQMFEQNCMESSMQNYPSTRSPSLSSH

PGLTTTCCSRRSKKTTHLPNSNLPATRLRSMQELSTIHIQGSEQPSLTTSRSSLNLKADDGLRPN

CKTSQITTAIISIPTPPALTPEGESRPPPASPGPNTNIPSIASNVVKVSAL

---

What is claimed is:

1. An isolated polynucleotide comprising the polynucleotide sequence set forth in SEQ ID NO:1.

2. The isolated polynucleotide of claim 1 wherein the polynucleotide consists of the polynucleotide sequence set forth in SEQ ID NO:1.

3. An isolated polynucleotide that encodes a polypeptide comprising the amino acid sequence of SEQ ID NO:2.

4. The isolated polynucleotide of claim 1 wherein the polynucleotide encodes the polypeptide of SEQ ID NO:2.

5. A vector comprising the isolated polynucleotide of claim 3.

6. An isolated host cell comprising the vector of claim 5.

7. A process for producing a polypeptide comprising the amino acid sequence of SEQ ID NO:2 comprising culturing the host cell of claim 6 and recovering the polypeptide from the culture.

8. A membrane of a recombinant host cell of claim 7 expressing said polypeptide.

* * * * *